(12) United States Patent
Takahashi et al.

(10) Patent No.: US 9,388,099 B2
(45) Date of Patent: *Jul. 12, 2016

(54) PROCESS FOR PRODUCING 2,3,3,3-TETRAFLUOROPROPENE

(71) Applicant: DAIKIN INDUSTRIES, LTD., Osaka (JP)

(72) Inventors: Kazuhiro Takahashi, Settsui (JP); Yuzo Komatsu, Settsu (JP); Akinori Ueda, Settsu (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/695,116

(22) Filed: Apr. 24, 2015

(65) Prior Publication Data

US 2015/0259266 A1    Sep. 17, 2015

Related U.S. Application Data

(63) Continuation of application No. 13/879,668, filed as application No. PCT/JP2011/075365 on Oct. 27, 2011, now Pat. No. 9,040,760.

(60) Provisional application No. 61/407,158, filed on Oct. 27, 2010.

(51) Int. Cl.
*C07C 17/25* (2006.01)
*C07C 17/20* (2006.01)
(Continued)

(52) U.S. Cl.
CPC .............. *C07C 17/25* (2013.01); *C07C 17/087* (2013.01); *C07C 17/20* (2013.01); *C07C 17/206* (2013.01);
(Continued)

(58) Field of Classification Search
CPC .............................. C07C 17/25; C07C 17/206
See application file for complete search history.

(56) References Cited

FOREIGN PATENT DOCUMENTS

| EP | 2 103 587 | 9/2009 |
|---|---|---|
| GB | 772484 | 4/1957 |

(Continued)

OTHER PUBLICATIONS

"All Alloys at High Performance Alloys"; Publication date 2007, pp. 1-3.*

(Continued)

*Primary Examiner* — Jafar Parsa
*Assistant Examiner* — Medhanit Bahta
(74) *Attorney, Agent, or Firm* — Wenderoth, Lind & Ponack, L.L.P.

(57) ABSTRACT

This invention provides a process for producing 2,3,3,3-tetrafluoropropene, the process comprising: (1) a first reaction step of reacting hydrogen fluoride with at least one chlorine-containing compound selected from the group consisting of a chloropropane represented by Formula (1): $CClX_2CHClCH_2Cl$, wherein each X is the same or different and is Cl or F, a chloropropene represented by Formula (2): $CClY_2CCl=CH_2$, wherein each Y is the same or different and is Cl or F, and a chloropropene represented by Formula (3): $CZ_2=CClCH_2Cl$, wherein each Z is the same or different and is Cl or F in a gas phase in the absence of a catalyst while heating; and (2) a second reaction step of reacting hydrogen fluoride with a reaction product obtained in the first reaction step in a gas phase in the presence of a fluorination catalyst while heating. According to the process of this invention, 2,3,3,3-tetrafluoropropene (HFO-1234yf) can be obtained with high selectivity, and catalyst deterioration can be suppressed.

8 Claims, 1 Drawing Sheet

(51) Int. Cl.
*C07C 17/087* (2006.01)
*C12Q 1/68* (2006.01)
*G01N 21/64* (2006.01)

(52) U.S. Cl.
CPC ............ *C12Q 1/686* (2013.01); *G01N 21/6428* (2013.01); *G01N 21/6486* (2013.01); *G01N 2021/6439* (2013.01); *G01N 2201/061* (2013.01); *Y02P 20/582* (2015.11)

(56) References Cited

FOREIGN PATENT DOCUMENTS

| JP | 2009-227675 | 10/2009 |
|---|---|---|
| WO | 2007/079431 | 7/2007 |
| WO | 2008/054781 | 5/2008 |
| WO | 2008054781 | 5/2008 |
| WO | 2009/003084 | 12/2008 |
| WO | 2009003084 | 12/2008 |
| WO | 2009/158321 | 12/2009 |
| WO | 2010123148 | 10/2010 |

OTHER PUBLICATIONS

International Search Report and Written Opinion issued Mar. 20, 2012 in International (PCT) Application No. PCT/JP2011/075365.
Extended European Search Report dated Nov. 12, 2015, for European Patent Application No. 15176250.7.
Haszeldine, R.N., "Fluoro-olefins, Part II. Synthesis and Reactions of Some 3:3:3-Trihalogenopropenes," Journal of the Chemical Society, Jan. 1953, pp. 3371-3378.

* cited by examiner

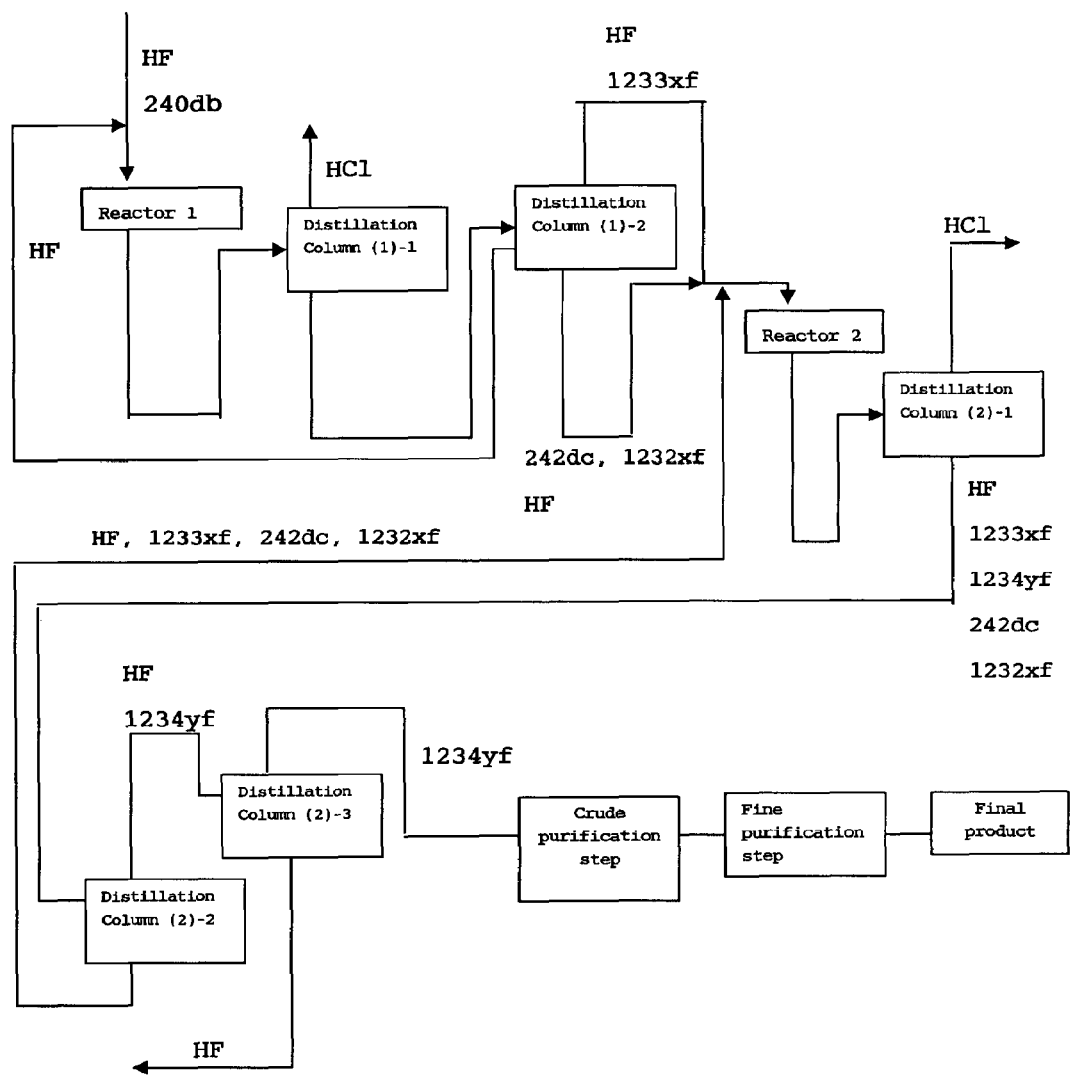

PROCESS FOR PRODUCING 2,3,3,3-TETRAFLUOROPROPENE

TECHNICAL FIELD

The present invention relates to a process for producing 2,3,3,3-tetrafluoropropene.

BACKGROUND ART

Alternative refrigerants such as HFC-125 ($C_2HF_5$) and HFC-32 ($CH_2F_2$) have been widely used as important replacements for CFC, HCFC, etc., which cause ozone layer depletion. However, these alternative refrigerants are potent global warming substances, thus creating concern that diffusion of the refrigerants would increase global warming. As a preventive measure, these refrigerants are recovered after use. However, complete recovery of the refrigerants is impossible. In addition, the diffusion of these refrigerants due to leakage, etc., cannot be ignored. The use of $CO_2$ or hydrocarbon-based substances as alternative refrigerants has also been investigated. However, because $CO_2$ refrigerants have low efficiency and devices using such refrigerants inevitably become large, $CO_2$ refrigerants have many problems in terms of the overall reduction of greenhouse gas emissions, including energy to be consumed. Furthermore, hydrocarbon-based substances pose safety problems due to their high flammability.

2,3,3,3-tetrafluoropropene (HFO-1234yf, $CF_3CF=CH_2$), which is an olefinic HFC having a low global warming potential, has recently been attracting attention as a material to solve the above problems. HFO-1234yf, used alone or in combination with other substances, such as hydrofluorocarbons, hydrofluoroolefins, and hydrochlorofluoroolefins, is expected to be useful as a refrigerant, and additionally as a blowing agent, propellant, extinguishing agent, or the like.

Some processes for producing HFO-1234yf have been disclosed. In most of these processes, a hydrohalopropane such as a hydrochloropropane or a hydrohalopropene such as a hydrochloropropene, used as a starting material, is fluorinated with hydrogen fluoride to ultimately prepare HFO-1234yf.

For example, Patent Literature 1 listed below discloses a process in which HFO-1234yf is produced, via a hydrochlorofluoroalkane or a hydrochlorofluoroalkene, by subjecting a haloalkane or a haloalkene as a starting material to fluorination with HF, dehydrochlorination, etc.

Patent Literature 2 listed below discloses a process in which HFO-1234yf is produced, via a hydrochlorofluoroalkane, hydrochlorofluoroalkene, etc., by subjecting a hydrochloropropane, hydrochlorofluoropropane, etc., as a starting material to fluorination with HF in the presence of a catalyst.

Furthermore, Patent Literature 3 listed below discloses an integration process for preparing HFO-1234yf by using 1,1,1,2,3-pentachloropropane (HCC-240db) as a starting material, fluorinating the starting material with HF to produce HCFO-1233xf, and then adding HF to the thus-obtained HCFO-1233xf to produce HCFC-244bb, followed by dehydrochlorination.

All of these processes use a hydrochlorocarbon as a starting material to prepare HFO-1234yf by a multiple-stage reaction process. However, each of the processes has a problem of a cost increase due to the use of a catalyst and also has a drawback of insufficient selectivity resulting from the formation of many products other than the desired product, i.e., HFO-1234yf. Further, the use of higher chlorinate as a starting material poses another problem in that catalyst activity is likely to deteriorate as reaction progresses.

CITATION LIST

Patent Literature

PTL 1: WO2007/079431
PTL 2: WO2008/054781
PTL 3: Japanese Unexamined Patent Publication No. 2009-227675

SUMMARY OF INVENTION

Technical Problem

The present invention has been accomplished in view of the foregoing state of the art and its primary object is to provide a production process that is capable of producing 2,3,3,3-tetrafluoropropene (HFO-1234yf) in good yield, using a chloropropane compound or chloropropene compound as a starting material, and that is suitable for use on an industrial scale.

Solution to Problem

The present inventors conducted extensive investigations to achieve the above object and found that selectivity of the desired 2,3,3,3-tetrafluoropropene (HFO-1234yf) can be improved, catalyst deterioration can be suppressed, and HFO-1234yf can be produced efficiently on an industrial scale according to a two-stage reaction process in which a chloropropane compound or chloropropene compound represented by a specific general formula, which is used as a starting material, is reacted with hydrogen fluoride in a gas phase in the absence of a catalyst while heating, and subsequently the product obtained by said reaction is reacted with hydrogen fluoride in a gas phase in the presence of a fluorination catalyst while heating. The present invention has been accomplished based on this finding.

More specifically, the present invention provides the following process for producing 2,3,3,3-tetrafluoropropene.

Item 1. A process for producing 2,3,3,3-tetrafluoropropene, the process comprising:

(1) a first reaction step of reacting hydrogen fluoride with at least one chlorine-containing compound selected from the group consisting of a chloropropane represented by Formula (1): $CClX_2CHClCH_2Cl$, wherein each X is the same or different and is Cl or F, a chloropropene represented by Formula (2): $CClY_2CCl=CH_2$, wherein each Y is the same or different and is Cl or F, and a chloropropene represented by Formula (3): $CZ_2=CClCH_2Cl$, wherein each Z is the same or different and is Cl or F in a gas phase in the absence of a catalyst while heating; and (2) a second reaction step of reacting a reaction product obtained in the first reaction step with hydrogen fluoride in a gas phase in the presence of a fluorination catalyst while heating.

Item 2. The process according to Item 1, wherein the reaction temperature in the first reaction step is 250 to 600° C., and the reaction temperature in the second reaction step is 200 to 500° C.

Item 3. The process according to Item 1 or 2, wherein the amount of hydrogen fluoride in the first reaction step is 1 to 100 moles per mole of the chlorine-containing compound used as a starting material, and the amount of hydrogen fluoride in the second reaction step is 1 to 50 moles per mole of the chlorine-containing compound used as a starting material in the first reaction step.

Item 4. The process according to any one of Items 1 to 3, wherein the fluorination catalyst used in the second reaction step is at least one member selected from the group consisting of chromium oxides, chromium oxyfluorides, aluminium fluorides, aluminum oxyfluorides, and metal fluorides.

Item 5. The process according to any one of Items 1 to 4, wherein after removing hydrogen chloride from the reaction product obtained in the first reaction step, the reaction product is used as a starting material in the second reaction step.

Item 6. The process according to any one of Items 1 to 5, wherein after reducing the amount of hydrogen fluoride contained in the reaction product obtained in the first reaction step, the reaction product is used as a starting material in the second reaction step.

Item 7. The process according to any one of Items 1 to 6, wherein the second reaction step uses, as a starting material, at least one chlorine-containing compound selected from the group consisting of a chloropropane represented by Formula (4): $CClX_2CHClCH_2Cl$, wherein at least one of X is F, a chloropropene represented by Formula (5): $CClY_2CCl=CH_2$, wherein at least one of Y is F, and a chloropropene represented by Formula (6): $CZ_2=CClCH_2Cl$, wherein at least one of Z is F, the chlorine-containing compound being contained in the reaction product obtained in the first reaction step.

Item 8. The process according to any one of Items 1 to 6, wherein the second reaction step uses, as a starting material, at least one chlorine-containing compound selected from the group consisting of $CF_2ClCHClCH_2Cl$(HCFC-242dc) and $CF_2ClCCl=CH_2$(HCFO-1232xf), the chlorine-containing compound being contained in the reaction product obtained in the first reaction step.

Item 9. The process according to any one of Items 1 to 8, wherein the first reaction step is conducted in a reactor made of an alloy containing 30% or more by weight of nickel.

Item 10. The process according to Item 9, wherein the alloy containing 30% or more by weight of nickel is at least one member selected from the group consisting of Hastelloy, Inconel, Monel, and Incolloy.

The process for producing 2,3,3,3-tetrafluoropropene of the present invention is described in detail below.

(1) Starting Compound

In the present invention, at least one chlorine-containing compound selected from the group consisting of a chloropropane represented by Formula (1): $CClX_2CHClCH_2Cl$, wherein each X is the same or different and is Cl or F, a chloropropene represented by Formula (2): $CClY_2CCl=CH_2$, wherein each Y is the same or different and is Cl or F, and a chloropropene represented by Formula (3): $CZ_2=CClCH_2Cl$, wherein each Z is the same or different and is Cl or F is used as a starting compound. When these chlorine-containing compounds are used as a starting material and reacted with hydrogen fluoride in a two-stage reaction process according to the conditions described below, the desired 2,3,3,3-tetrafluoropropene(HFO-1234yf) can be obtained with high selectivity as compared to the case in which fluorination reaction is conducted in a single-stage reaction process.

Among the starting compounds, specific examples of the chloropropane represented by Formula (1): $CClX_2CHClCH_2Cl$ include $CCl_3CHClCH_2Cl$(HCC-240db, bp. 179° C./760 mmHg, 51-53° C./3 mmHg), $CFCl_2CHClCH_2Cl$(HCFC-241db, bp. 157° C.), $CF_2ClCHClCH_2Cl$(HCFC-242dc, bp. 113-114° C.), and the like. Specific examples of the chloropropene represented by Formula (2): $CClY_2CCl=CH_2$ include $CCl_3CCl=CH_2$ (HCO-1230xf, bp. 128° C.), $CFCl_2CCl=CH_2$(HCFO-1231xf, bp. 98.5-99° C.), $CF_2ClCCl=CH_2$(HCFO-1232xf, bp. 57-58° C.), and the like. Specific examples of the chloropropene represented by Formula (3): $CZ_2=CClCH_2Cl$ include $CCl_2=CClCH_2Cl$(HCO-1230xa, bp. 138° C.), $CFCl=CClCH_2Cl$(HCFO-1231xb), $CF_2=CClCH_2Cl$ (HCFO-1232xc), and the like.

Among these starting compounds, HCC-240db ($CCl_3CHClCH_2Cl$ (1,1,1,2,3-pentachloropropane)), HCO-1230xf($CCl_3CCl=CH_2$(2,3,3,3-tetrachloropropene)), and HCO-1230xa ($CCl_2=CClCH_2Cl$ (1,1,2,3-tetrachloropropene)) are particularly advantageous starting compounds in that they are readily available and inexpensive.

In the present invention, the starting compounds can be used singly or in combination of two or more.

(2) Production Process

In the present invention, it is necessary to adopt a two-stage reaction process comprising a first reaction step of reacting at least one of the aforementioned starting compounds with hydrogen fluoride in a gas phase in the absence of a catalyst while heating, and a second reaction step of reacting the reaction product obtained in the first reaction step with hydrogen fluoride in a gas phase in the presence of a fluorination catalyst while heating. The use of such a two-stage reaction process enables the improvement of selectivity of the desired 2,3,3,3-tetrafluoropropene(HFO-1234yf) and further enables the suppression of deterioration of a catalyst used in the fluorination process.

Each reaction step will be described below in detail.

(i) First Reaction Step

In the first reaction step, at least one of the above starting compounds is reacted with hydrogen fluoride in a gas phase in the absence of a catalyst while heating.

In the first reaction step, the reaction of the starting compound with hydrogen fluoride under such conditions yields a product containing 2-chloro-3,3,3-trifluoropropene (HCFO-1233xf) that is an intermediate for 2,3,3,3-tetrafluoropropene (HFO-1234yf).

The first reaction step requires the reaction of the starting compound with hydrogen fluoride in a gas phase in the absence of a catalyst. As long as the starting compound and hydrogen fluoride come into contact with each other in a gas phase within the reaction temperature range descried below, the starting compound may be in a liquid form when supplied. For example, when the starting compound is liquid at an ordinary temperature and ordinary pressure, the starting compound is vaporized using a vaporizer (vaporization region), passed through a preheating region, and then supplied to a mixing region wherein the starting compound is contacted with anhydrous hydrogen fluoride, whereby the reaction can be conducted in a gas phase. The reaction may also be carried out by supplying the starting compound in a liquid phase to a reactor, and vaporizing the compound when the compound enters a reaction temperature range to react with hydrogen fluoride. There is no particular limitation to, the methods for vaporizing the starting compound in the reaction temperature range. The starting compound may be vaporized into a gas phase by, for example, filling a reaction tube with a material that exhibits excellent thermal conductivity, exerts no catalytic activity in the reaction of the present invention, and is stable to hydrogen fluoride, such as metal pieces of corrosion-resistant materials including nickel beads, alumina beads, Hastelloy, Inconel, Monel, Incolloy, and the like, so as to homogenize the temperature distribution within the reaction tube; heating the reaction tube to not less than the vaporization temperature of the starting compound; and supplying the starting compound in a liquid phase thereinto.

Hydrogen fluoride may generally be supplied to a reactor in a gas phase together with the starting compound. The amount of the hydrogen fluoride supplied is generally about 1 to about 100 moles, preferably about 5 to about 50 moles, and more preferably about 15 to about 25 moles, per mol of the aforementioned starting compound. By setting the amount within such a range, the conversion of the starting compound and the selectivity of components, such as 2-chloro-3,3,3-trifluoropropene (HCFO-1233xf), that can be intermediates for 2,3,3,3-tetrafluoropropene (HFO-1234yf), can be maintained in a desirable range.

The starting compound may be supplied to the reactor as is or may be diluted with an inert gas such as nitrogen, helium, or argon and then supplied to the reactor.

The form of the reactor used in the first reaction step is not particularly limited. Examples of usable reactors include a fistulous adiabatic reactor, or an adiabatic reactor packed with a porous or nonporous metal or medium that improves the gas-phase mixing state between hydrogen fluoride and the starting material. Also usable is a multitubular reactor or the like in which a heating medium is used to cool the reactor and to homogenize the temperature distribution within the reactor. When fistulous reactors are used in the method using a reaction tube having a small inner diameter to improve the heat transfer efficiency, the relationship of the flow rate of the starting compound to the inner diameter of the reaction tube, for example, is preferably adjusted so as to achieve a high linear velocity and a large heating area.

The reactor is preferably made of an alloy containing 30% or more by weight of nickel. More specifically, a reactor formed of a material that is resistant to the corrosive action of hydrogen fluoride, such as Hastelloy, Inconel, Monel, and Incolloy, is preferably used.

In the first reaction step, the reaction temperature, i.e., the temperature in the reactor, is about 250° C. to about 600° C., preferably about 300° C. to about 500° C., and more preferably about 350° C. to about 450° C. If the reaction temperature is higher than this range, the selectivity of components, such as HCFO-1233xf, that can be intermediates for 2,3,3,3-tetrafluoropropene (HFO-1234yf) undesirably decreases. If the reaction temperature is lower than this range, the conversion of the starting compound undesirably decreases.

The pressure during the reaction is not particularly limited, as long as the starting compound and hydrogen fluoride can be present in the form of a gas phase, and the reaction may be conducted under ordinary pressure, increased pressure, or reduced pressure. More specifically, the first reaction step may be conducted under reduced pressure or atmospheric pressure (0.1 MPa). This step also may be conducted under increased pressure at which the starting material does not turn into a liquid phase.

The reaction time is not particularly limited. However, the residence time, which is represented by V/Fo, may be generally adjusted to a range of about 1 to about 10 sec. V/Fo is the ratio of the reaction space V (cc) in a gas phase to the total flow rate Fo (flow rate at 0° C., 0.1 MPa: cc/sec) of the starting material gases (starting compound, hydrogen fluoride and inert gas) supplied to the reaction system.

Under the above reaction conditions, a reaction product that contains 2-chloro-3,3,3-trifluoropropene (HCFO-1233xf) can be obtained at the reactor outlet.

(ii) Second Reaction Step

In the second reaction step, the product obtained in the first reaction step is used as a starting material to be reacted with hydrogen fluoride in a gas phase in the presence of a fluorination catalyst while heating.

The product obtained in the first reaction step contains 2-chloro-3,3,3-trifluoropropene (HCFO-1233xf) as a main component and also contains at least one chlorine-containing compound selected from the group consisting of a chloropropane represented by Formula (4): $CClX_2CHClCH_2Cl$, wherein at least one of X is F, a chloropropene represented by Formula (5): $CClY_2CCl=CH_2$, wherein at least one of Y is F, and a chloropropene represented by Formula (6): $CZ_2=CClCH_2Cl$, wherein at least one of Z is F. More specifically, the reaction product also contains a chloropropane compound or a chloropropene compound, such as 1,2,3-trichloro-1,1-difluoropropane (HCFC-242dc) and 2,3-dichloro-3,3-difluoropropene (HCFO-1232xf). When the product containing the chloropropane compound, chloropropene compound, or the like is used as is as a starting material and reacted with hydrogen fluoride in the presence of a fluorination catalyst in the second reaction step, not only HCFO-1233xf but also the components contained in the product, such as HCFC-242dc and HCFO-1232xf, can be converted to 2,3,3,3-tetrafluoropropene (HFO-1234yf). As a result, the desired HFO-1234yf can be obtained with high selectivity. Above all, in the present invention, at least one of HCFC-242dc and HCFO-1232xf is preferably used together with HCFO-1233xf as the starting material in the second reaction step.

Moreover, since a fluorination catalyst is used only in the second reaction step, catalyst deterioration is significantly suppressed relative to the amount of produced HFO-1234yf, as compared to the case in which HFO-1234yf is produced by a single-stage fluorination reaction. This ensures an economically excellent production process.

In contrast, it is not favorable that only HCFO-1233xf is separated from the product obtained in the first reaction step and used in a reaction for synthesizing HFO-1234yf, while other components, such as a chloropropane compound and chloropropene compound, are recycled as the starting material in the first reaction step, because the selectivity of HCFO-1233xf in the first reaction step is unexpectedly decreased, resulting in the decrease in overall selectivity of HFO-1234yf.

As a fluorination catalyst used in the second reaction step, a known catalyst having activity to fluorination reaction with hydrogen fluoride may be used. For example, metal oxides or metal oxyfluorides, such as chromium oxides, chromium oxyfluorides, aluminium fluorides, and aluminum oxyfluorides, may be used. In addition to these catalysts, metal fluorides, such as $MgF_2$, $TaF_5$, and $SbF_5$, also may be used.

Among these catalysts, the chromium oxides, for instance, are not particularly limited. For example, it is preferable to use chromium oxide represented by the composition formula: $CrO_m$, wherein preferably $1.5<m<3$, more preferably $2<m<2.75$, and even more preferably $2<m<2.3$. Any chromium oxide catalysts in the form of powder, pellets, etc., can be used, as long as they are suitable for the reaction. In particular, pellet-form catalysts are preferred. The above chromium oxide catalysts can be produced, for example, by the process disclosed in Japanese Unexamined Patent Publication No. H5-146680.

In addition, the fluorinated chromium oxides can be prepared by the process disclosed in Japanese Unexamined Patent Publication No. H5-146680. For example, they can be prepared by fluorinating the chromium oxide obtained by the above-described process with hydrogen fluoride (HF treatment).

The degree of fluorination is not particularly limited. For example, a fluorinated chromium oxide having a fluorine content of about 10 to about 45% by weight may be suitably used.

Further, the chromium-based catalyst disclosed in Japanese Unexamined Patent Publication No. H11-171806 also may be used as a chromium oxide catalyst or fluorinated chrome oxide catalyst. The chromium-based catalyst is in an amorphous state and comprises, as a main component, a chromium compound containing at least one metallic element selected from the group consisting of indium, gallium, cobalt, nickel, zinc, and aluminum. The chromium in the chromium compound has an average valence number of not less than +3.5 and not more than +5.0.

The above-described fluorination catalyst may be used as supported on a carrier such as alumina and activated carbon.

Anhydrous hydrogen fluoride used as a starting material may be generally supplied to a reactor in the form of a gas phase together with the reaction product obtained in the first reaction step. The amount of hydrogen fluoride supplied in the second reaction step may be determined based on the amount of said at least one chlorine-containing compound selected from the group consisting of a chloropropane represented by Formula (1): $CClX_2CHClCH_2Cl$, a chloropropene represented by Formula (2): $CClY_2CCl{=}CH_2$, and a chloropropene represented by Formula (3): $CZ_2{=}CClCH_2Cl$, used as a starting material in the first reaction step. Specifically, the amount of hydrogen fluoride is about 1 to about 50 moles, preferably about 5 to about 30 moles, and more preferably about 7 to about 15 moles, per mole of said at least one chlorine-containing compound. The amount of hydrogen fluoride supplied in the second reaction step is preferably within the above-described range and smaller than the amount of hydrogen fluoride actually supplied in the first reaction step.

When the amount of hydrogen fluoride contained in the reaction product obtained in the first reaction step is within the aforementioned range, a fluorination reaction in the second reaction step can be conducted by using only the reaction product without adding further hydrogen fluoride. When the amount of hydrogen fluoride contained in the reaction product obtained in the first reaction step is larger than the aforementioned range, the reaction product may be used as a starting material in the second reaction step after reducing the amount of hydrogen fluoride contained therein by a method such as distillation.

The selectivity of 2,3,3,3-tetrafluoropropene (HFO-1234yf) can be maintained in a desirable range by using anhydrous hydrogen fluoride within the above-described range in the presence of a fluorination catalyst.

To maintain catalyst activity for a long period of time, oxygen may be supplied to the reactor as entrained with the aforementioned starting material, especially in the second reaction step. In this case, the amount of oxygen to be supplied may be about 0.01 to about 0.3 mole per mole of the chlorine-containing compound supplied as a starting material in the first reaction step.

The form of the reactor used in the second reaction step is not particularly limited. Examples of usable reactors include an adiabatic reactor packed with a catalyst and a multitubular reactor in which a heating medium is used to cool the reactor. As in the first reaction step, a reactor formed of a material that is resistant to the corrosive action of hydrogen fluoride, such as Hastelloy, Inconel, and Monel, is preferably used.

In the second reaction step, the reaction temperature, i.e., the temperature in the reactor, is about 200° C. to about 500° C., preferably about 300° C. to about 450° C., and more preferably about 350° C. to about 400° C. If the reaction temperature is higher than this range, the selectivity of HFO-1234yf undesirably decreases. If the reaction temperature is lower than this range, the conversion of the starting compound undesirably decreases. In particular, the reaction temperature in the second reaction step is preferably within the above-described range and lower than that in the first reaction step.

The pressure during the reaction is not particularly limited, and the reaction may be conducted under ordinary pressure or increased pressure. More specifically, the reaction in the present invention may be conducted under atmospheric pressure (0.1 MPa), and may be also conducted under an increased pressure up to about 1.0 MPa.

The reaction time is not particularly limited. However, the contact time, which is represented by W/Fo, may be generally adjusted to a range of about 5 to about 20 g·sec/cc. W/Fo is the ratio of the amount of packed catalyst W(g) to the total flow rate of the starting material gases supplied to the reactor in the second reaction step (total amount of product obtained in the first reaction step and HF) Fo (flow rate at 0° C., 1 atm: cc/sec).

In the second reaction step, the product obtained in the first reaction step may be supplied as is but is preferably supplied in the second reaction step after removing hydrogen chloride contained therein. Due to this, the effects of reducing energy loss caused by handling hydrogen chloride that is unnecessary in the second reaction step and improving the selectivity of HFO-1234yf can be expected. Methods for removing hydrogen chloride from the product obtained in the first reaction step are not particularly limited. For example, hydrogen chloride can be easily removed as a column top product by distillation.

As described above, when the product obtained in the first reaction step contains more than the amount of hydrogen fluoride required in the second reaction step, it may be supplied to the reactor in the second reaction step after removing excessive hydrogen fluoride from the product obtained in the first reaction step to reduce the content of hydrogen fluoride. Methods for removing hydrogen fluoride are also not particularly limited. For example, according to a method for separating hydrogen fluoride by distillation or a method for extracting a phase substantially consisting of hydrogen fluoride by liquid-liquid separation, the amount of hydrogen fluoride contained in the product can be reduced by a simple method.

(3) Reaction Product:

According to the aforementioned process comprising two-stage reaction steps, a reaction product that contains the desired 2,3,3,3-tetrafluoropropene (HFO-1234yf) can be obtained with high selectivity at the reactor outlet in the second reaction step. The obtained HFO-1234yf can be purified and collected by distillation, etc.

In the production process of the present invention, the reaction product contains not only HFO-1234yf but also other components, such as hydrogen chloride, unreacted hydrogen fluoride, and $CF_3CCl{=}CH_2$(HCFO-1233xf). In addition to these components, the reaction product may contain a chlorofluoropropane compound, chlorofluoropropene compound, etc., such as $CFCl_2CHClCH_2Cl$(HCFC-241db), $CFCl_2CCl{=}CH_2$(HCFO-1231xf), $CF_2ClCHClCH_2Cl$ (HCFC-242dc), $CF_2ClCCl{=}CH_2$(HCFO-1232xf), and $CF_3CHClCH_2Cl$(HCFC-243db). These compounds are produced as a precursor for HFO-1234yf according to the type of starting material used or reaction conditions, and can be reused as a starting material in the first reaction step or second reaction step. In particular, when HCFO-1233xf, HCFO-1232xf, or HCFC-242dc is reused as a starting material in the second reaction step, the desired HFO-1234yf can be obtained with high selectivity.

FIG. 1 is a flowchart that shows one embodiment of the process of the present invention, which is a process comprising a step of producing HFO-1234yf according to the process of the present invention and a subsequent purification step.

In the process shown in FIG. 1, 1,1,1,2,3-pentachloropropane (HCC-240db) is used as a starting material and supplied to a reactor (1) together with hydrogen fluoride to conduct the reaction of the first reaction step in the absence of a catalyst. The product obtained from the reactor (1) is sent to a distillation column (1)-1 to remove hydrogen chloride as a column top product. After that, other components are sent to a distillation column (1)-2 to remove excessive hydrogen fluoride as a column bottom product, and then the remainder is supplied to a reactor (2). The hydrogen fluoride separated in the distillation column (1)-2 can be recycled by sending it to the reactor (1) and reused as a starting material.

In the reactor (2), the reaction of the product obtained from the first reaction step with hydrogen fluoride in the presence of a fluorination catalyst is conducted as the second reaction step. After removing hydrogen chloride as a column top product in a distillation column (2)-1, the product obtained from the reactor (2) is sent to a distillation column (2)-2 to remove unreacted products and by-products, such as hydrogen fluoride, HCFO-1233xf, HCFC-242dc, and HCFO-1232xf, and other components are sent to a distillation column (2)-3. The removed hydrogen fluoride, HCFO-1233xf, HCFC-242dc, HCFO-1232xf, etc., can be reused as a starting material for the reactor (2).

In the distillation column (2)-3, the desired 2,3,3,3-tetrafluoropropene (HFO-1234yf) can be obtained by removing hydrogen fluoride as a column bottom product. The hydrogen fluoride obtained in the distillation column (2)-3 can be sent to the reactor (1) and reused as a starting material.

The desired HFO-1234yf obtained in the distillation column (2)-3 can be further subjected to a crude purification step and a fine purification step to yield a final product. Specific methods for the crude purification step and the fine purification step are not particularly limited. For example, water washing, dehydration (drying), distillation, liquid separation or other means can be applied to the steps.

Advantageous Effects of Invention

According to the process for producing 2,3,3,3-tetrafluoropropene of the present invention, 2,3,3,3-tetrafluoropropene (HFO-1234yf) can be obtained with high selectivity, and catalyst deterioration can be suppressed. Accordingly, the process of the present invention is highly useful as a process for producing 2,3,3,3-tetrafluoropropene that is suitable for use on an industrial scale.

BRIEF DESCRIPTION OF DRAWINGS

FIG. 1 is a flowchart showing one embodiment of the process of the present invention.

DESCRIPTION OF EMBODIMENTS

An Example is given below to illustrate the present invention in more detail.

Example 1

(1) First Reaction Step

A ½-inch pipe made of Inconel (inner diameter: 1.02 cm) equipped with a ⅛-inch thermometer protection tube made of Inconel (outer diameter: 0.32 cm) was used as a reaction tube and was packed with nickel beads (diameter: 3 mm) that were inactive to the reaction. The packed nickel bead bed length was 19.5 cm, and the space volume of the packed bed of nickel beads was 7.5 cm³.

To this reaction tube, 1,1,1,2,3-pentachloropropane (HCC-240db) and anhydrous hydrogen fluoride were continuously supplied at a rate of 2.4 cc/min (flow rate at 0° C. and 0.1 MPa) and at a rate of 47 cc/min (flow rate at 0° C. and 0.1 MPa), respectively. The temperature inside the reaction tube was set at 400° C. and the pressure inside the reaction tube was set at atmospheric pressure (0.1 MPa).

The molar ratio of HF to HCC-240db was 20, and the residence time (V/Fo), which is the ratio of the space volume (V) of the packed bed of nickel beads to the total flow rate (Fo) of HCC-240db and HF, was 8.0 sec.

Effluents obtained from the reactor 65 hours after the start of reaction were analyzed by gas chromatography. The conversion of HCC-240db was 100%. Table 1 below shows the selectivity of each component.

TABLE 1

| Component | Selectivity (%) |
| --- | --- |
| HCFO-1233xf | 88 |
| HCFC-242dc | 8.1 |
| HCFO-1232xf | 2.8 |
| Others | 1.1 |

(2) Treatment for Removing Hydrogen Chloride and Hydrogen Fluoride

Hydrogen chloride was removed from the product obtained in the first reaction step by distillation, and further, distillation was conducted to reduce the amount of hydrogen fluoride. A commonly used distillation column was used for distillation for removing the HCl. The column had a theoretical plate number of 20, a column top pressure of 0.7 MPa, a column top temperature of –42° C., and a column bottom temperature of 62° C. A distillation column used for reducing the amount of HF had a theoretical plate number of 30, an operating pressure of 0.2 MPa, a column top temperature of 47° C., and a column bottom temperature of 74° C. From the top of this distillation column, organic matter mainly including HF and HFO-1233xf was extracted. From the bottom of the column, organic matter mainly including HCFC-242dc was extracted. From the middle portion of the column, HF was extracted. The composition of column top products and column bottom products after distillation was analyzed by gas chromatography and by titration with NaOH aqueous solution. The results are shown in Table 2 below.

TABLE 2

| | Distillation column material balance (mol/hr) | | | |
| --- | --- | --- | --- | --- |
| Component | Feed | Top of the column | Middle portion of the column | Bottom of the column |
| HF | 1.676 | 0.959 | 0.699 | 0.018 |
| HCFO-1233xf | 0.084 | 0.084 | trace | trace |
| HCFC-242dc | 0.0077 | trace | trace | 0.0077 |
| HCFO-1232xf | 0.0027 | trace | trace | 0.0027 |
| Others | 0.001 | trace | trace | 0.001 |

(3) Second Reaction Step

A tubular reactor made of Hastelloy having an inner diameter of 15 mm and a length of 1 m was packed with 22 g of a fluorinated chromium oxide catalyst (fluorine content: about 15.0%) that had been obtained by subjecting chromium oxide to fluorination treatment. The fluorinated chromium oxide catalyst was prepared by the following procedure. First, 114 g of 10% ammonia water was added to 765 g of a 5.7% aqueous solution of chromium nitrate. After the resulting precipitate was filtered and washed, it was dried in air for 12 hours at 120° C. to give a chromium hydroxide. The chromium hydroxide was formed into pellets having a diameter of 3.0 mm and a height of 3.0 mm and calcined in a nitrogen stream for two hours at 400° C. A reactor made of Hastelloy C was filled with the obtained chromium oxide in the form of pellets. Increasing the temperature gradually from 200 to 360° C., the chromium oxide was heated and fluorinated with dilute HF in which hydrogen fluoride had been diluted to 20 vol % with nitrogen. After the temperature reached 360° C., the chromium oxide was further fluorinated with 100% HF to prepare the fluorinated chromium oxide catalyst.

The temperature inside the reaction tube was set at 365° C., and the pressure inside the reaction tube was set at atmospheric pressure (0.1 MPa). Anhydrous hydrogen fluoride (HF) gas was supplied to the reactor at a flow rate of 118 cc/min (flow rate at 0° C., 0.1 MPa; the same applies hereinafter), oxygen gas was fed to the reactor at a flow rate of 2.2 cc/min, and these reaction conditions were maintained for one hour. After that, the mixture of the compounds obtained as column top and column bottom products in the treatment for removing hydrogen fluoride described above (molar ratio of HCFO-1233xf:HCFC-242dc:HCFO-1232xf is 89:8.1:2.9) was supplied to the reactor at a flow rate of 12.7 cc/min.

At that point, the molar ratio of the HF to the starting material supplied to the reactor in the second reaction step was 9.3:1. The ratio (W/Fo) of the amount of packed catalyst W(g) to the total flow rate of the starting material gases supplied to the reactor in the second reaction step (total amount of column top products in step (2) and HF) Fo (flow rate at 0° C., 0.1 MPa: cc/sec) was 9.9.

Effluents obtained from the reactor 28 hours after the start of reaction were analyzed by gas chromatography. The conversion of HCFO-1233xf supplied to the reactor in the second reaction step was 24%, and the conversion of HCFC-242dc and HCFO-1232xf supplied to the reactor in the second reaction step was 100%. Table 3 below shows the composition of the organic matter obtained at the reactor outlet.

TABLE 3

| Component | Composition at the reactor outlet (%) |
|---|---|
| HFO-1234yf | 15 |
| HFC-245cb | 3.3 |
| HCFC-242dc | 0 |
| HCFO-1232xf | 0 |
| HCFO-1233xf | 76 |
| Others | 5.7 |

From the above results, it was confirmed that according to the production process of the present invention, HFO-1234yf can be obtained with high selectivity. Other components can be recycled as a starting material in the first or second reaction step.

The invention claimed is:

1. A process for producing 2,3,3,3-tetrafluoropropene, the process comprising:
    a reaction step of reacting a starting material with hydrogen fluoride in a gas phase in the presence of a fluorination catalyst while heating,
    wherein the starting material comprises $CF_3CCl=CH_2$ (HCFO-1233xf) and at least one of $CF_2ClCHClCH_2Cl$ (HCFC-242dc) and $CF_2ClCCl=CH_2$ (HCFO-1232xf).

2. The process according to claim 1, wherein the reaction temperature in the reaction step is 200 to 500° C.

3. The process according to claim 1, wherein the fluorination catalyst used in the reaction step is at least one member selected from the group consisting of chromium oxides, chromium oxyfluorides, aluminium fluorides, aluminum oxyfluorides, and metal fluorides.

4. The process according to claim 2, wherein the fluorination catalyst used in the second reaction step is at least one member selected from the group consisting of chromium oxides, chromium oxyfluorides, aluminium fluorides, aluminum oxyfluorides, and metal fluorides.

5. The process according to claim 1, wherein the fluorination catalyst used in the reaction step is a chromium oxide.

6. The process according to claim 5, wherein the chromium oxide is represented by the composition formula: $CrOm$, wherein $1.5<m<3$.

7. The process according to claim 5, wherein the chromium oxide is a fluorinated chromium oxide having a fluorine content of about 10 to about 45% by weight.

8. The process according to claim 1, wherein the 2,3,3,3-tetrafluoropropene is selectively obtained by the reaction step.

* * * * *